(12) United States Patent
Nagel

(10) Patent No.: US 8,097,854 B2
(45) Date of Patent: Jan. 17, 2012

(54) PRODUCTION METHOD FOR A SURFACE SENSOR, SYSTEM AND USE OF A SURFACE SENSOR

(75) Inventor: Michael Nagel, Viersen (DE)

(73) Assignee: Dritte Patentportfolio Beteiligungsgesellschaft mbH & Co. KG, Schönefeld/Waltersdorf (DE)

( * ) Notice: Subject to any disclaimer, the term of this patent is extended or adjusted under 35 U.S.C. 154(b) by 0 days.

(21) Appl. No.: 12/933,565

(22) PCT Filed: Mar. 23, 2009

(86) PCT No.: PCT/EP2009/053376
§ 371 (c)(1),
(2), (4) Date: Sep. 20, 2010

(87) PCT Pub. No.: WO2009/118287
PCT Pub. Date: Oct. 1, 2009

(65) Prior Publication Data
US 2011/0017910 A1    Jan. 27, 2011

(30) Foreign Application Priority Data
Mar. 28, 2008    (DE) .......................... 10 2008 016 294

(51) Int. Cl.
*G01J 5/02*    (2006.01)
(52) U.S. Cl. ................................... 250/341.1
(58) Field of Classification Search .......... 250/330–335, 250/336.1–336.2, 337, 338.1–338.5, 339.01–339.15, 250/340, 341.1–341.8
See application file for complete search history.

(56) References Cited

U.S. PATENT DOCUMENTS

| 2004/0227089 | A1* | 11/2004 | Kolodzey et al. | ......... 250/341.8 |
| 2006/0152430 | A1 | 7/2006 | Seddon et al. | |
| 2006/0180762 | A1* | 8/2006 | Kolodzey et al. | ......... 250/341.1 |
| 2006/0231625 | A1 | 10/2006 | Cumming et al. | |
| 2007/0114431 | A1 | 5/2007 | Wang et al. | |

FOREIGN PATENT DOCUMENTS

| DE | 10257225 B3 | 4/2004 |
| JP | 64-001304 A | 1/1989 |
| WO | 2007110810 A1 | 10/2007 |

OTHER PUBLICATIONS

Raspopin et al., "A frequency-selective terahertz radiation detector based on a semiconductor superlattice with a resonator," 2002, IEEE, The science and technology of nano and molecular electronics: physics, simulation, and expermental characterization, pp. 107-109.*

(Continued)

*Primary Examiner* — Kiho Kim
(74) *Attorney, Agent, or Firm* — Panitch, Schwarze Belisario & Nadel LLP

(57) ABSTRACT

The invention relates to a surface sensor (100, 200), comprising a frequency-selective surface with periodically arranged THz structures (1), in particular THz resonance structures (1) which are sensitive to THz radiation, a polarization axis (3) being associated with each structure. In order to improve remote field characteristics, the invention provides for a THz structure (1) to be configured asymmetrically, and a group of two or more THz structures (1) to have essentially centrosymmetrically aligned polarization axes (3) for forming a unit cell.

15 Claims, 8 Drawing Sheets

Centrosymmetry -> polarization-independence

Centrosymmetrical unit cell by double mirroring, angle of 45° between the symmetry axis and the polarization axis 10: centrosymmetrical unit cell
2a, 2b: resonator element
3: polarization axis
4a, 4b: symmetry axis

OTHER PUBLICATIONS

Winnewisser et al., "Frequency-selective surfaces analyzed by THz-Time-Domain Spectroscopy,", 1998, IEEE Sixth International Conference on Terahertz electronics Proceedings, pp. 196-198.*

Azad et al, "Transmission properties of terahertz pulses through subwavelength double split-ring resonators", Optics Letters, vol. 31, No. 5, pp. 634-636 (2006).

Baena et al, "Equivalent-Circuit Models for Split-Ring Resonators and Complementary Split-Ring Resonators Coupled to Planar Transmission Lines", IEEE Transactions on Microwave Theory and Techniques, vol. 53, No. 4, pp. 1451-1461 (2005).

Brucherseifer et al, "Label-free probing of the binding state of DNA by time-domain terahertz sensing", Appled Physics Letters, vol. 77, No. 24, pp. 4049-4051 (2000).

Chen et al, "Absorption coefficients of selected explosives and related compounds in the range of 0.1-2.8 THz", Optics Express, vol. 15, No. 19 (2007).

Chen et al, "Ultrafast optical switching of terahertz metamaterials fabricated on ErAs/GaAs nanoisland superlattices", Optics Letters, vol. 32, No. 12, pp. 1620-1622 (2007).

Driscoll et al, "Tuned permeability in terahertz split-ring resonators for devices and sensors", Applied Physics Letters, vol. 91 (2007).

Fischer et al, "Terahertz time-domain spectroscopy and imaging of artificial RNA", Optics Express, vol. 13, No. 14, pp. 5205-5212 (2005).

German Search Report Issued Sep. 18, 2008 in German Application No. 102008016294.9.

Grischkowsky et al, "Far-infrared time-domain spectroscopy with terahertz beams of dialectrics and semiconductors", Journal of the Optical Society of America, vol. 7, No. 10, pp. 2006-2015 (1990).

Kafesaki et al, "Left-handed metamaterials: detailed numerical studies of the transmission properties", Journal of Optics A: Pure and Applied Optics, vol. 7, pp. S12-S22 (2005).

Markelz et al, "THz time domain spectroscopy of biomolecular conformational modes", Physics in Medicine and Biology, vol. 47, pp. 3797-3805 (2002).

Nagel et al, "Integrated planar terahertz resonators for femtomolar sensitivity label-free detection of DNA hybridization", Applied Optics, vol. 41, No. 10, pp. 2074-2078 (2002).

O'Hara et al, "Effects of Microstructure Variations on Macroscopic Terahertz Metafilm Properties", Active and Passive Electronic Components, vol. 2007, No. 49691, pp. 1-10 (2007).

O'Hara et al, "Thin-film sensing with planar terahertz metamaterials: sensitivity and limitations", Optics Express, vol. 16, No. 3, pp. 1786-1795 (2008).

Padilla et al, "Dynamical Electric and Magnetic Metamaterial Response at Terahertz Frequencies", Physical Review Letters, vol. 96, No. 107401, pp. 1-4 (2006).

Pendry et al, "Magnetism from Conductors, and Enhanced Non-Linear Phenomena", pp. 1-21 (1999).

Siegel, "Terahertz Technology in Biology and Medicine" IEEE Transactions on Microwave Theory and Techniques, vol. 52, No. 10, pp. 2438-2447 (2004).

Yoshida et al, "Terahertz sensing method for protein detection using a thin metallic mesh", Applied Physics Letters, vol. 91, No. 253901 pp. 1-3 (2007).

Zhang et al, "Waveguide terahertz time-domain spectroscopy of nanometer water layers", Optics Letters, vol. 29, No. 14, pp. 1617-1619 (2004).

International Search Report and Written Opinion issued on Aug. 26, 2009 in International Application No. PCT/EP2009/053376.

Debus et al., "Frequency selective surfaces for high sensitivity terahertz sensing," Applied Physics Letters, vol. 91, No. 18, pp. 184102, (2007).

Debuse et al., "Frequency Selective Surfaces for High-Sensitivity Terahertz Sensors," Conference on Lasers and Electro-Optics IEEE, pp. 1205-1206, (2007).

Palit et al., "Toward Artificial Magnetism Using Terahertz Split Ring Resonator Metamaterials," Lasers & Electro-Optics Society, IEEE, pp. 248-249 (2006).

English translation of Int'l Preliminary Report on Patentability and Written Opinion issued on Oct. 5, 2010 in Int'l Application No. PCT/EP2009/053376.

Azad et al., "Characterization and analysis of terahertz metamaterials based on rectangular split-ring resonators", Applied Physics Letters No. 92 (2008).

Baras et al, "On-Chip THz Detection of Biomaterials: A Numerical Study", Journal of Biological Physics, vol. 29, pp. 187-194 (2003).

Barber et al, "Temperature-Dependent Far-Infrared Spectra of Single Crystals of High Explosives Using Terahertz Time-Domain Spectroscopy", Journal of Physical Chemistry, vol. 109, pp. 3501-3505 (2005).

Brown et al, "Optical attenuation signatures of *Bacillus subtillis* in the THz region", Applied Physics Letters, vol. 84, No. 18, pp. 3438-3440 (2004).

De Feijter et al, "Ellipsometry as a Tool to Study the Adsorption Behavior of Synthetic and Biopolymers at the Air-Water Interface", Biopolymers, vol. 17, pp. 1759-1772 (1978).

Fischer et al, "Far-infrared vibrational modes of DNA components studied by terahertz time-domain spectroscopy", Physics in Medicine and Biology, vol. 47, pp. 3807-3814 (2002).

Lee et al, "Chemically-Specific Probes for the Atomic Force Microscope", Israel Journal of Chemistry, vol. 36, pp. 81-87 (1996).

Nagel et al, "A functionalized THz sensor for marker-free DNA analysis", Physics in Medicine and Biology, vol. 48, pp. 3625-3636 (2003).

Tiang et al, "Electromagnetic simulation of terahertz frequency range filters for genetic sensing", Journal of Applied Physics, vol. 100, No. 066105 (2006).

Woolard et al, "Terahertz Frequency Sensing and Imaging: A Time of Reckoning Future Applications?", Proceedings of the IEEE, vol. 93, No. 10, pp. 1722-1743 (2005).

* cited by examiner

Fig. 4: planar resonator on substrate having the metal edges released

Releasing the metal edges -> capacitance reduction -> increase of sensitivity

Cross-sectional view

5: metal layer
6: substrate (dielectric)
7: removed substrate volume

Cross-sectional view

5: metal layer
6: substrate (dielectric)
7: removed substrate volume
9: passivation layer (applied prior to etching)
9a: selectively chemically bound capture molecule layer Cross-sectional view 5: metal layer
6: substrate (dielectric)
7: removed substrate volume
11: passivation layer (applied after underetching)
9a: selectively chemically bound capture molecule layer

PRODUCTION METHOD FOR A SURFACE SENSOR, SYSTEM AND USE OF A SURFACE SENSOR

CROSS-REFERENCE TO RELATED APPLICATIONS

This application is a Section 371 of International Application No. PCT/EP2009/053376, filed Mar. 23, 2009, which was published in the German language on Oct. 1, 2009, under International Publication No. WO 2009/118287 A8 and the disclosure of which is incorporated herein by reference.

BACKGROUND OF THE INVENTION

The invention relates to a surface sensor, comprising a frequency-selective surface with periodically arranged THz structures sensitive to terahertz radiation (THz radiation), in particular THz resonator structures each having an associated polarization axis. The invention further relates to a method of producing a surface sensor. The invention moreover relates to a system having a surface sensor, as well as a use of the surface sensor.

Periodic antenna structures in the microwave range or other electromagnetically active periodic structures are known, for example, from US 2007/011431 A1 or US 2006/0152430 A1. A THz measurement unit equipped with a single THz structure for molecular analysis is known from DE 102 57 225 B3.

A surface sensor of the type cited above is usually formed on a substrate, the surface of which is provided with periodically arranged THz structures, i.e. structures which are sensitive to THz radiation. Usually, these structures are configured as THz resonators which are sensitive to emitting and/or detecting THz radiation in a specific resonant range. A frequency-selective surface with symmetrical THz resonators is for example known from the article by O'Hara et al., "Thin-film sensing with planar terahertz metamaterials: sensitivity and limitations" in OPTICS EXPRESS Vol. 16, No. 3, pages 1786 et seq. (Feb. 4, 2008).

Further publications on the general background of THz technology are:

P. H. Siegel, "Terahertz technology in biology and medicine", IEEE Trans. Microwave Theory Tech. 52, 2438 (2004).
E. R. Brown, J. E. Bjarnason, T. L. J. Chan, A. W. M. Lee, and M. A. Cells, "Optical attenuation signatures of *Bacillus subtillis* in the THz region", Appl. Phys. Lett. 84, 3438-3440 (2004).
D. L. Woolard, E. R. Brown, M. Pepper, and M. Kemp, "Terahertz frequency sensing an imaging: A time of reckoning future applications?", Proc. IEEE 93, 1722-1743 (2005).
J. Barber, D. E. Hooks, D. J. Funk, R. D. Averitt, A. J. Taylor, and D. Babikov, "Temperature-dependent far-infrared spectra of single crystals of high explosives using terahertz time-domain spectroscopy", J. Phys. Chem. A 109, 3501 (2005).
J. Chen, Y. Chen, H. Zhao, G. J. Bastiaans, and X.-C. Zhang, "Absorption coefficients of selected explosives and related compounds in the range of 0.1-2.8 THz", Opt. Express 19, 12060 (2007).
B. M. Fischer, M. Walther, and P. Uhd Jepsen, "Far-infrared vibrational modes of DNA components studied by terahertz time-domain spectroscopy", Phys. Med. Biol. 47, 3807-3814 (2002).
J. Zhang, and D. Grischkowsky, "Waveguide terahertz time-domain spectroscopy of nanometer water layers", Opt. Lett. 29, 1617 (2004).
M. Nagel, P. Haring-Bolivar, M. Brucherseifer, H. Kurz, A. Bosserhoff, and R. Büttner, "Integrated planar terahertz resonators for femtomolar sensitivity label-free detection of DNA hybridization", Appl. Opt. 41, 2074 (2002).
M. Nagel, F. Richter, P. Haring-Bolivar, and H. Kurz, "A functionalized THz sensor for marker-free DNA analysis", Phys. Med. Biol. 48, 3625 (2003).
C. K. Tiang, J. Cunningham, C. Wood, I. C. Hunter, and A. G. Davies, "Electromagnetic simulation of terahertz frequency range filters for genetic sensing", J. Appl. Phys. 100, 066105-1-3 (2006).
T. Baras, T. Kleine-Ostmann, and M. Koch, "On-chip THz detection of biomaterials: a numerical study", J. Biol. Phys. 29, 187 (2003).
M. Bruchseifer, M. Nagel, P. Haring-Bolivar, H. Kurz, A. Bosserhoff, and R. Büttner, "Label-free probing of the binding state of DNA by time-domain terahertz sensing", Appl. Phys. Lett. 77, 4049 (2000).
T. Driscoll, G. O. Andreev, D. N. Basov, S. Palit, S. Y. Cho, N. M. Jokrest, and D. R. Smith, "Tuned permeability in terahertz split-ring resonators for devices and sensors", Appl. Phys. Lett. 91, 062511 (2007).
C. Debus and P. Haring-Bolivar, "Frequency selective surfaces for high sensitivity terahertz sensing", Appl. Phys. Lett. 91, 184102 (2007).
M. Kafesaki, Th. Koschny, R. S. Penciu, T. F. Gundogdu, E. N. Economou, and C. M. Soukoulis, "Left-handed metamaterials: detailed numerical studies of the transmission properties", J. Opt. A: Pure Appl. Opt. 7, p. 12 (2005).
A. K. Azad, J. Dai, and W. Zhang, "Transmission properties of terahertz pulses through sub-wavelength double split-ring resonators", Opt. Lett. 31, 634 (2006).
D. Grischkowsky, S. Keiding, M. van Exter, and Ch. Fattinger, "Far-infrared time-domain spectroscopy with terahertz beams of dielectrics and semiconductors", J. Opt. Soc. Am. B 7, 2006 (1990).
W. H. Padilla, A. J. Taylor, C. Highstrete, Mark Lee, and R. D. Averitt, "Dynamical electric and magnetic metamaterial response at terahertz frequencies", Phys. Rev. Lett. 96, 107401 (2006).
J. P. Pendry, A. J. Holden, D. J. Robbins, and W. J. Stewart, "Magnetism from conductors and enhanced nonlinear phenomena", IEEE Trans. Microwave Theory Tech. 47, 2075 (1999).
J. D. Baena, J. Bonache, F. Martin, R. Marqués Sillero, F. Falcone, T. Lopetegi, M. A. G. Laso, J. García-García, I. Gil, M. F. Portillo, and M. Sorolla, "Equivalent-circuit models for split-ring resonators and complementary split-ring resonators coupled to planar transmission lines", IEEE Trans. Microwave Theory Tech. 53, 1451 (2005).
J. F. O'Hara, E. Smirnova, A. K. Azad, H.-T. Chen, and A. J. Taylor, "Effects of microstructure variations on macroscopic terahertz metafilm properties", Active and Passive Electronic Components 2007, 49691 (2007).
J. A. Defeijter, J. Benjamins, F. A. Veer, "Ellipsometry as a tool to study adsorption behavior of synthetic and biopolymers at air-water-interface", Biopolymers 17, 1759-1772 (1978).
Markelz, S. Whitmire, and J. Hillebrecht et al., "THz time-domain spectroscopy of biomolecular conformational modes", Phys. Med. Biol. 47, 3797-3805 (2002).
B. M. Fischer, M. Hoffmann, H. Helm, et al., "Terahertz time-domain spectroscopy and imaging of artificial RNA", Opt. Express 13, 5205-5215 (2005).

A. K. Azad, A. J. Taylor, E. Smirnova, and J. F. O'Hara, "Characterization and analysis of terahertz metamaterials based on rectangular split-ring-resonators", Appl. Phys. Lett. 92, 011119 (2008).

H.-T- Chen, W. J. Padilla, J. M. O. Zide, S. R. Bank, A. C. Gossard, A. J. Taylor, and R. D. Averitt, "Ultrafast optical switching of terahertz metamaterials fabricated on ErAs/GaAs nanoisland superlattices", Opt. Lett. 32, 1620-1622 (2007).

M. A. Cooper, Drug Discovery Today 11, 1061 (2006).

SRU Biosystems, Inc., www.srubiosystems.com

Biacore Life Sciences, www.biacore.com

G. U. Lee, L. A. Chrisey, E. E. O'Ferrall, D. E. Pilloff, N. H. Turner, R. J. Colton, Israel J. Chem. 36, 81-87 (1996).

Biomolecules such as DNA, proteins and the like are known to have binding-specific properties in the THz frequency range. THz resonators can be used to read out a property at the highest possible sensitivity. A surface with periodically arranged resonators can be read out in a particularly easy manner.

Such an arrangement is known under the term frequency-selective surface (FSS) as initially defined. An FSS, as a rule, is comprised of metallic resonator structures. Examples of resonator structures with symmetrically constructed TH resonators are known for example from the articles by Yoshida, "Terahertz sensing method for protein detection using a thin metallic mesh", APPLIED PHYSICS LETTERS 91, 253901 (2007) and Driscoll et al., "Tuned permeability in terahertz split-ring resonators for devices and sensors", APPLIED PHYSICS LETTERS 91, 062511 (2007). An FFS possesses frequency-dependent transmission and reflection properties tailored to the respective application, and they are used for example as reflectors in antenna systems, or else utilized for radar camouflage, e.g. of combat aircraft or the like.

The simplest resonator structure is a wire dipole having a length of $\lambda/2$. The equivalent electric circuit diagram of such a resonator is a resonant LC circuit. If this element is resonantly excited by an external field, a current oscillating at a resonance frequency fr will flow through the wire. A surface with periodically arranged wire dipoles or dipoles of other configurations hence virtually acts in resonance like a closed metallic surface and shows a maximum reflection—in case of zero loss R(fr)=1 and T(fr)=0. In this case, the resonance frequency of a single element formed from a THz structure, respectively a THz resonator, deviates from that of the entire array due to coupling effects. The typical FSS applications as a rule require the flattest possible "gap-free" frequency-response curve. The FSS application for detecting e.g. biological samples having a low material volume is relatively new. The approach is based on the fundamental property of resonant structures to locally "store" the excitation energy for a certain period of time, and thus to enable a strongly increased interaction with the sample material as compared to simple transmission. The sensor response to a deposited material consists in a shift of one or more resonance frequencies of the FSS.

Actual numerical simulations such as those in the article by C. Debus et al., "Frequency selective surfaces for high sensitivity terahertz sensing", APPLIED PHYSICS LETTERS 91, 184102 (2007), have shown that the frequency anomaly occurring between two adjacent interfering resonances in the form of a zero in the reflectance spectrum responds particularly sensitive to the slightest changes in the dielectric environment. A simple way of generating such a frequency anomaly is to break the symmetry within the unit cell of the FSS. Asymmetrically split-ring resonators (aSRR) such as in the article of Debus et al. cited above, likewise take advantage of this effect.

Basically, split-ring resonators are for example known from other fields of application of electromagnetic resonators, such as e.g. from US 2007/0114431 or JP 64001304A.

Apart from this, there are a plurality of approaches for marker-free biomolecule detection. Although extremely interesting in the economical and technical respect, none of these methods have hitherto been able to prevail over the established label-based method. Marker-free detection methods inter alia exist on the basis of:

optical surface plasmons,
resistive techniques,
mechanical sensors,
acoustical wave sensors,
optically sampled nanoparticle sensors.

Each of the above-mentioned methods has its own advantages and disadvantages. A varying weighting, however, can establish that the previous methods mentioned above have one or more deficiencies in the following fields: sensitivity, cost efficiency, compactness, probe rate, ease of operation, measurement accuracy, fault tolerance.

FSS as a whole have shown to be an impressive alternative to avoiding the above-mentioned deficiencies. However, the FSS discussed above having asymmetrically split-ring resonators have to date shown a strong dependence on the polarization direction of the incident readout beam. This polarization dependency poses a problem for the technical application, since each misadjustment could erroneously be interpreted as a sensor response—hence there is a high cross-sensitivity. FSS having completely symmetrical resonator elements such as those of the initially cited articles, do not have this polarization dependency when at a sufficiently low enough spacing, but in this case also lack the necessary resonance indifference required to achieve a sufficiently high enough sensor sensitivity.

It would be desirable to realize a sufficiently high enough sensor sensitivity along with polarization independence.

BRIEF SUMMARY OF THE INVENTION

The invention starts at this point, and the task thereof is to indicate a surface sensor, a production method, a system and use, in which a sensor response is largely independent of readout beam polarization and which nevertheless yields a comparatively high sensor sensitivity.

As far as the surface sensor is concerned, the invention solves this task by means of a surface sensor of the type cited at the outset in which, according to the invention, a THz structure is configured asymmetrically, and a group of two or more THz structures have essentially centrosymmetrically aligned polarization axes for forming a unit cell.

The invention has recognized that forming a unit cell comprised of centrosymmetrically aligned aSRRs achieves a sensor surface having resonance indifference which has no polarization dependency. In particular, the surface sensor thus comprises an array of a plurality of unit cells, wherein each unit cell comprises a number of THz structures having essentially centrosymmetrically aligned polarization axes.

Advantageously, the object of the invention thereby offers a distinctly lower cross-sensitivity in comparison to previous FSS structures.

The invention is also directed toward a method for producing a surface sensor of the type discussed above. According to the invention, a frequency-selective surface with periodically arranged THz structures sensitive to THz radiation is formed in such a production method by applying a THz structure to a surface by means of an inkjet process, and a capture molecule, in particular biological, is applied by means of an inkjet process.

In other words, the inventive concept utilizes inkjet printing systems within the framework of the production method for producing the FSS sensor surface. The invention has recognized that both the, preferably metallic, resonator structures, and the, preferably biological, capture molecules may be deposited on the substrate surface using inkjet printing systems.

Thus, a system having a surface sensor of the type discussed above may also be provided in a particularly advantageous manner.

According to the inventive concept, the surface sensor serves in a particularly suited manner as a biosensor. The inventive concept leads in particular to the use of the surface sensor for marker-free biomolecule detection by means of THz radiation.

The use may be further advantageously employed in biological applications and/or for medical and/or diagnostic applications and/or for verification of a value document.

Advantageous further developments of the invention can be taken from the dependent claims and detail advantageous options in realizing the concept discussed above within the framework of the stated problem as well as with respect to further advantages.

One particularly preferred further development of the invention provides for the THz structure to be planar, in particular a THz structure metallically formed on a dielectric substrate. In this case, it has shown to be particularly advantageous for the THz structure to be released from the substrate at least at one edge. Advantageously, the edge is a slot edge.

The releasing of the THz structure from the substrate may be accomplished for example by undercutting. Doing so thus largely prevents an overly strong precharging of the THz structure by the substrate and simultaneously achieves a field magnification at the edge. This leads to the THz structure being particularly sensitive—and that independent of a precharging by the substrate—to an applied thin layer to be detected. In other words, a capture molecule at an edge provided with a strong field magnification proves to be particularly sensitive to the detection of molecules—and that at resonance characteristics that are largely independent of the substrate.

In a particularly preferred further development, the THz structure is passivated except on one edge in such a manner that binding of a capture molecule is suppressed or prevented relative the edge. This has the further advantage that the capture molecules only bind in the immediate area of the edge, since a field interaction can only take place in this area due to the passivation of the remaining area. The releasing of the edge thus offers a simple way to achieve a location-selective binding of capture molecules.

For this purpose, the passivation can advantageously be realized in the form of a passivation layer. The THz structure can advantageously be formed as a metallic structure. The metallic surface may be covered for example with a non-precious metallic or an electrically insulating passivation layer which suppresses or prevents the chemical binding of the capture molecules.

A passivation layer may be applied within the framework of the production method both before and after the releasing of the edge. In the former case, this will advantageously have the consequence that a passivation layer is formed on the THz structure, respectively only on the THz structure. In the latter case, a passivation layer is formed on and inside the THz structure.

Exemplary embodiments of the invention will now be described below based on the drawing. Same is used to illustrate the exemplary embodiments not necessarily true to scale, rather the drawing is realized in a schematized and/or slightly distorted manner wherever useful for the explanation. With respect to the extensions of the teachings directly recognizable from the drawing, reference is made to the pertinent prior art. In this case, it has to be borne in mind that manifold modifications and variations concerning the form and the detail of an embodiment can be made without departing from the general idea of the invention. The features of the invention disclosed in the description, the drawing and the claims can be essential for the further development of the invention both taken individually and in any combination thereof. Moreover, any combinations of at least two of the features disclosed in the description, the drawing and/or the claims will fall under the scope of the invention. The general idea of the invention is not restricted to the exact form or the detail of the preferred embodiment shown and described in the following, or to a subject matter which would be restricted compared to the subject matter claimed in the claims. In the case of indicated dimensional ranges, values lying within the mentioned limits are also disclosed as limiting values and can be used and claimed in any desired manner.

BRIEF DESCRIPTION OF THE SEVERAL VIEWS OF THE DRAWINGS

The foregoing summary, as well as the following detailed description of the invention, will be better understood when read in conjunction with the appended drawings. For the purpose of illustrating the invention, there are shown in the drawings embodiments which are presently preferred. It should be understood, however, that the invention is not limited to the precise arrangements and instrumentalities shown.

In the drawings.

DETAILED DESCRIPTION OF THE INVENTION

Figure 1:
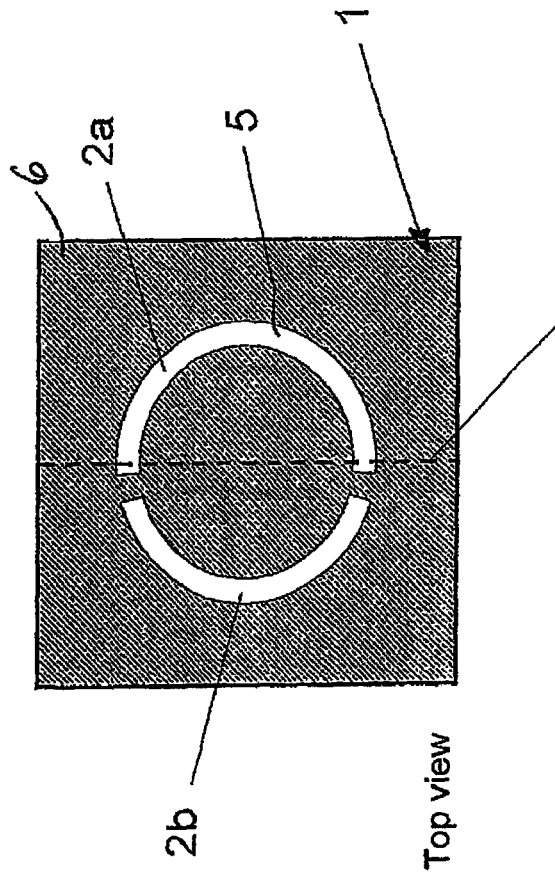
FIG. 1 is a 1 an asymmetrical THz structure for a unit cell of an array of a frequency-selective surface in a surface sensor according to a particularly preferred embodiment.

The embodiments discussed in the present case offer a technical solution for the marker-free detection of biomolecular samples.

For this purpose, the inventive concept explained in more detail in the embodiments of FIGS. 1 to 4 provides a surface sensor 100, 200 comprising a frequency-selective surface with periodically arranged THz structures, in the present case in the form of THz resonator structures, sensitive to THz radiation. Each THz resonator structure has an associated polarization axis 3. For simplicity reasons, the same reference numerals will be used below for identical or similar features or features of an identical or similar function. The surface sensor 100, 200 in the present case is formed on a substrate 6, the frequency-selective surface of which allows the detection of chemical binding, respectively deposition of biological molecules without the aid of marker molecules. For this purpose, the substrate surface is equipped with periodically arranged unit cells 10. Each unit cell 10 is in this case formed from centrosymmetrically aligned THz planar structures—i.e. THz planar structures provided with centrosymmetrically aligned polarization axes 3—in the present case in the form of THz resonators 1. The THz structure 1 as such is configured asymmetrically, that is, the THz resonator structure 1 in the present case is made up of conducting partial rings 2a, 2b, each representing one slot resonator element.

Figure 2:
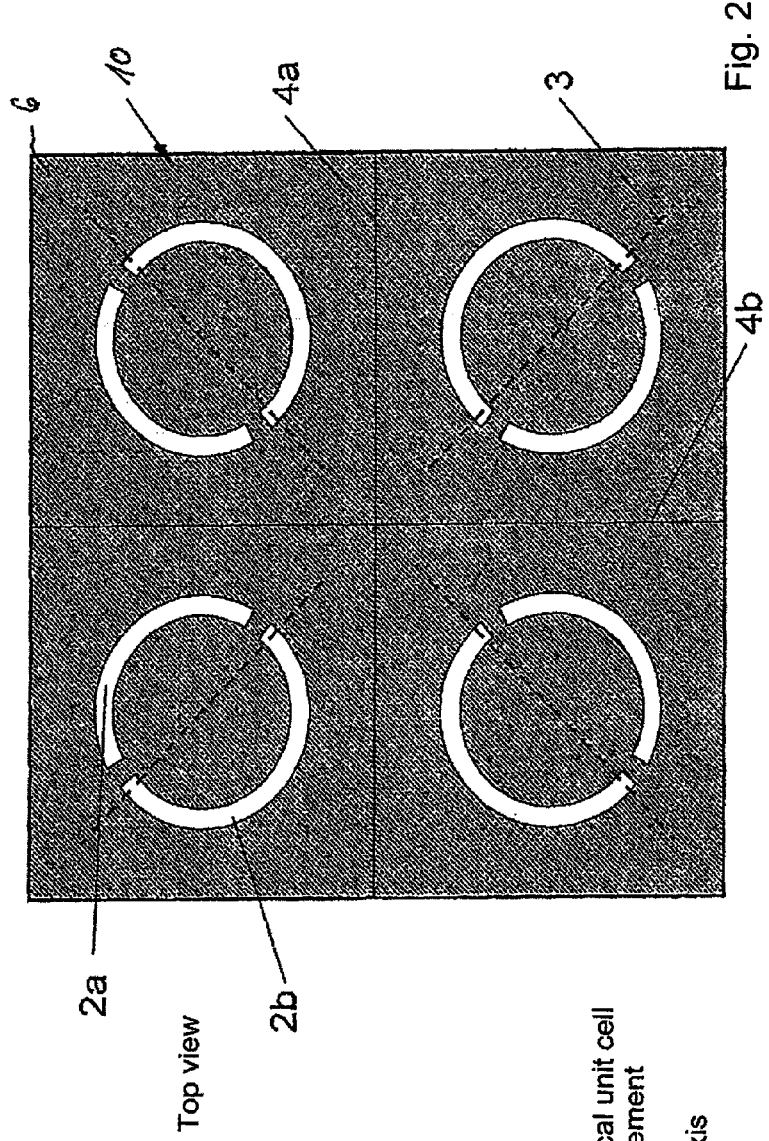
FIG. 2 is a centrosymmetrical unit cell such as is formed by double reflecting of THz structures of FIG. 1 in the preferred embodiment.

In the present case, one structure of the FIG. 2 array formed from unit cells 10 has resonance frequencies in the THz frequency range of between 0.1 and 10 THz. For forming the surface sensor 100, 200, the surfaces of the structures are equipped with biological capture molecules not shown in more detail which have specific binding properties. The detection of biological molecules with this array is realized as follows:

The unknown type of biomolecule binds to the known capture molecules which have determined positions assigned on the sensor surface. This binding process changes the resonance characteristics of the THz structures 1 in the unit cells 10 of the array of the frequency-selective surface. The detection of this binding process ensues by measuring this change of resonance characteristics. For this purpose, the sensor surface is irradiated with THz radiation. In this manner, the sensor signal can be acquired by measuring the transmission or reflection signal.

Figure 3:
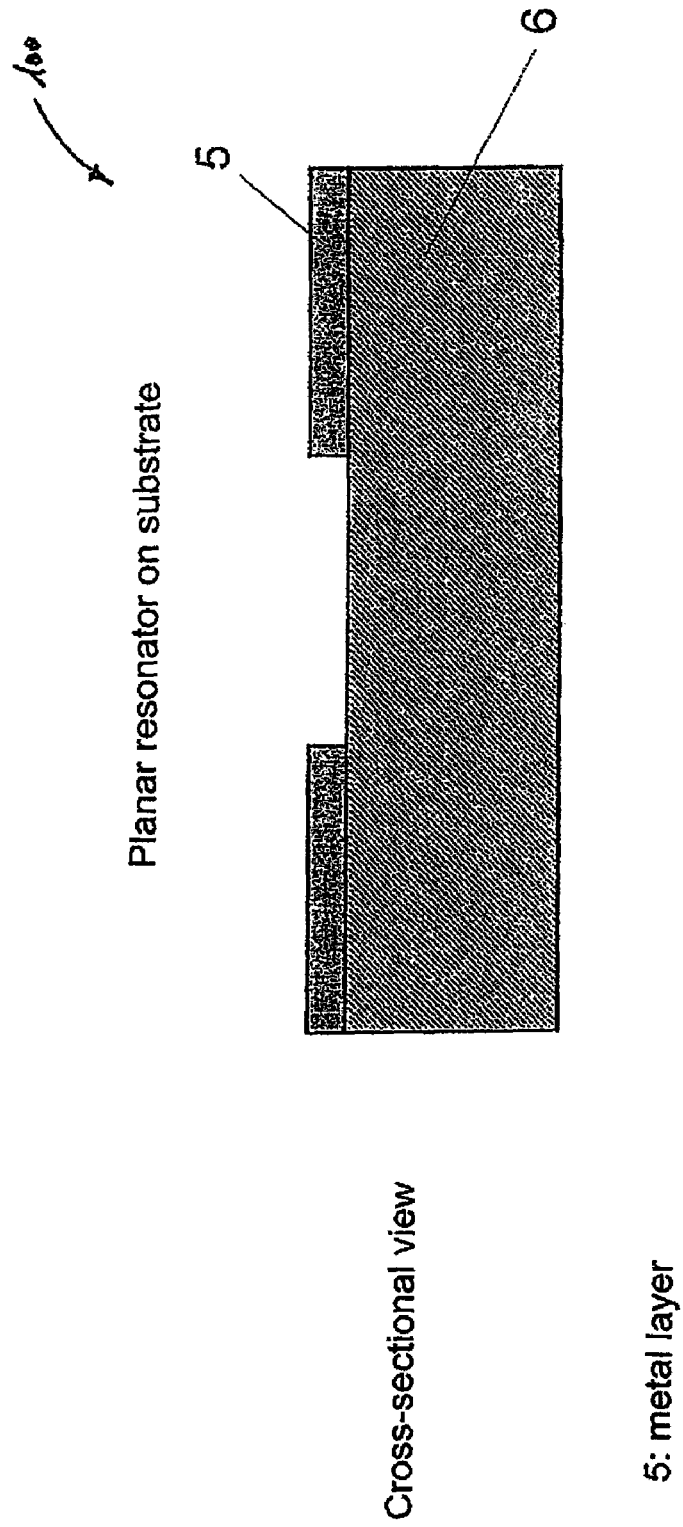
FIG. 3 is a side view of a THz structure in a surface sensor of a first further embodiment.

FIG. 3 shows a first embodiment of a surface sensor 100 in which a THz structure 1 in the form of a metal layer 5 is applied to a substrate 6 in the form of a dielectric material in the usual manner.

Figure 4:
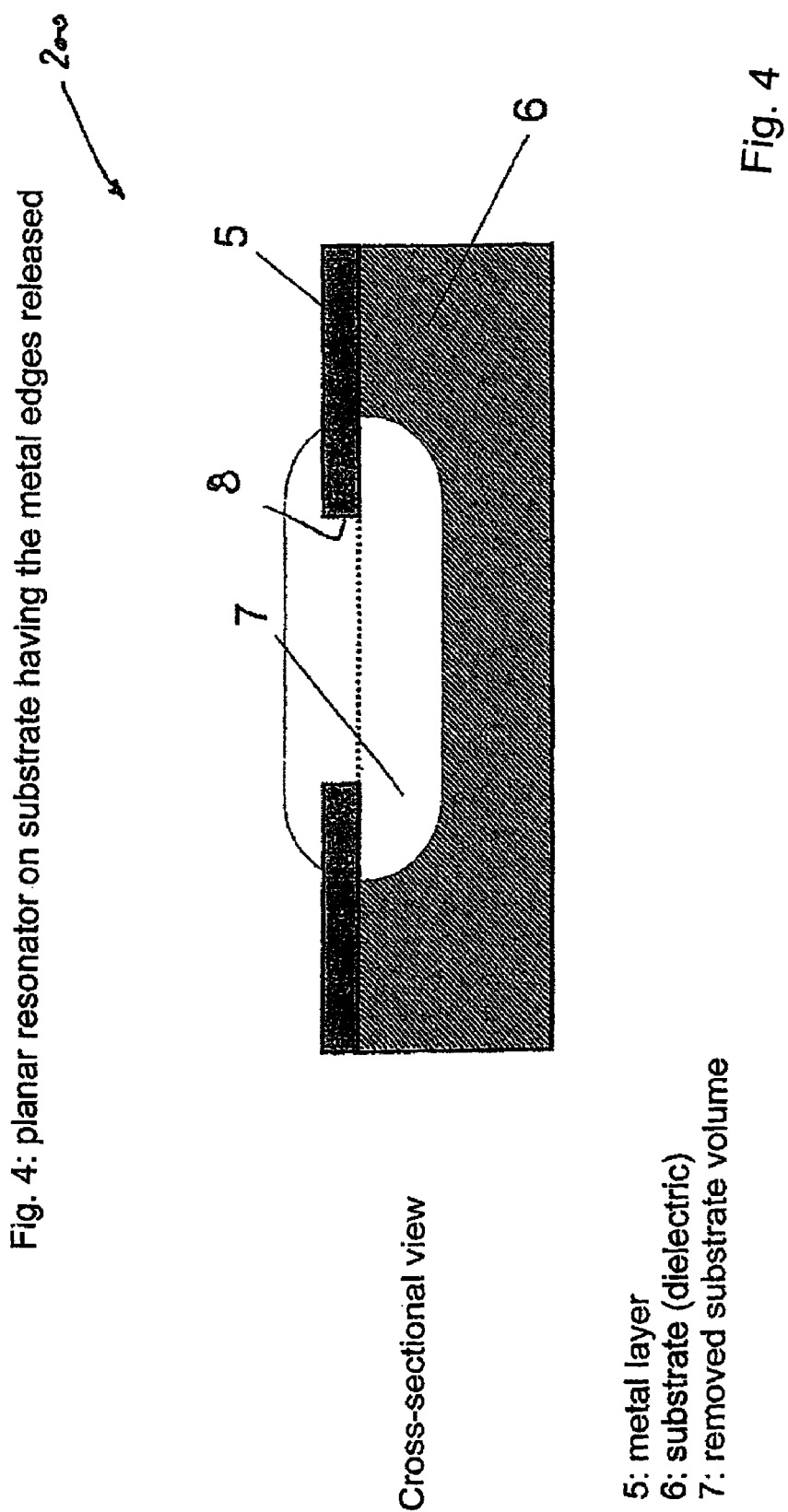
FIG. 4 is a side view of a THz structure in a second further embodiment of a surface sensor.
Figure 5:
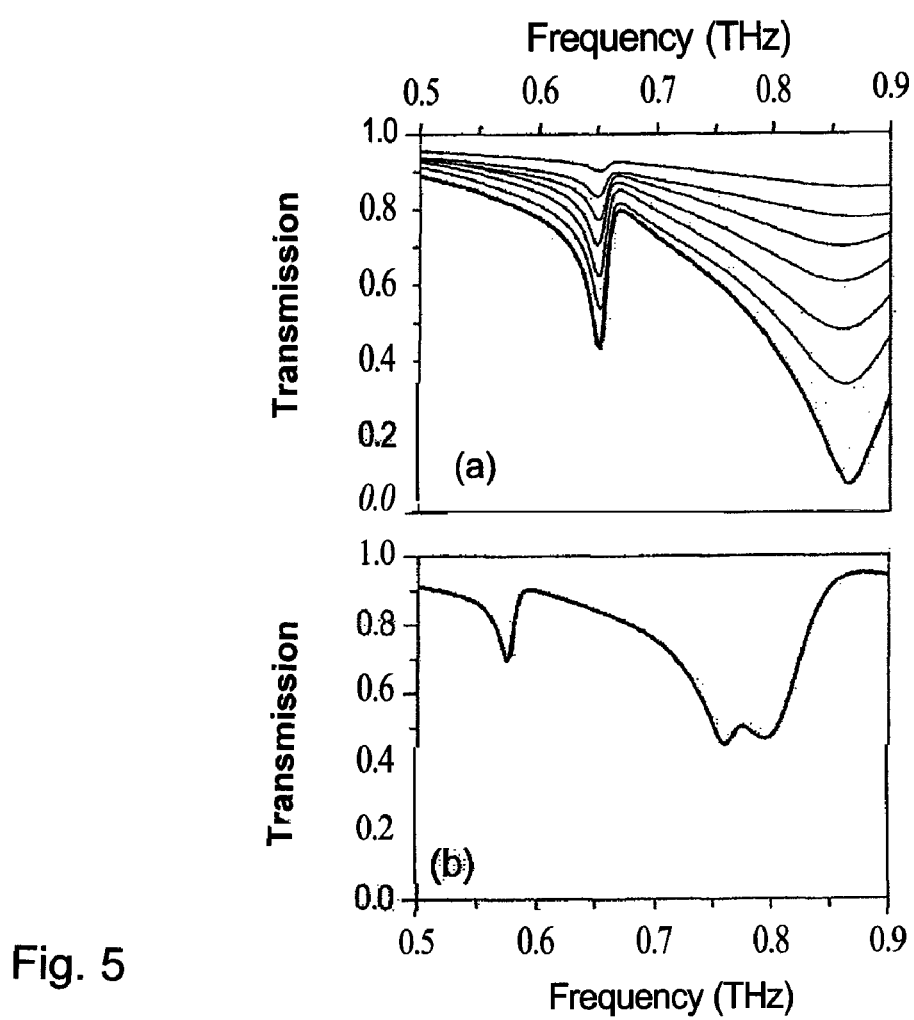
FIG. 5(a) is a transmission spectrum of an FSS according to FIG. 1 for different readout beam polarization directions.
FIG. 5(b) is the polarization-independent transmission spectrum of an FFS according to FIG. 2.
Figure 6:
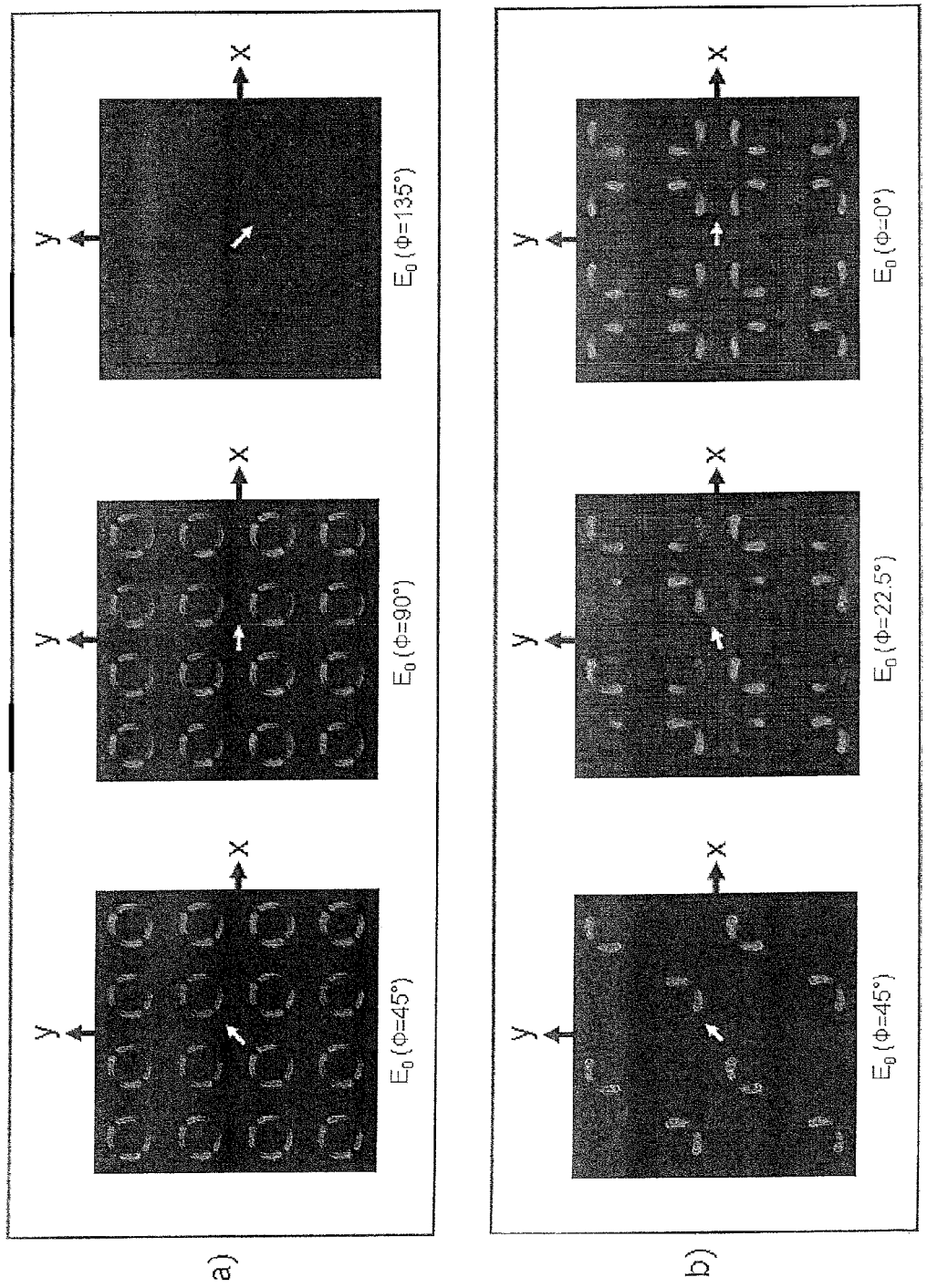
FIG. 6 is the field distribution of an FFS according to FIG. 1 for different readout beam polarization directions.

In a further development of this first embodiment, a second embodiment of a surface sensor 200 shown in more detail in FIG. 4 may be realized, in which a part of the substrate 6 is removed. Thereby, an edge, in the present case a slot edge 8 of the metal layer 5, is released relative the substrate 6 in a particularly advantageous manner. This can be advantageously achieved by undercutting the metal layer 5 in the area of the edge.

The releasing of the edge 8 enables the resonance characteristics of the THz resonance structure 1 to be determined largely independent of the substrate. Moreover, a field magnification forms in the area of the edge which makes the THz resonance structure 1 in this important area thereof sensitive with respect to deposited molecules or the like to be detected.

Figure 7:
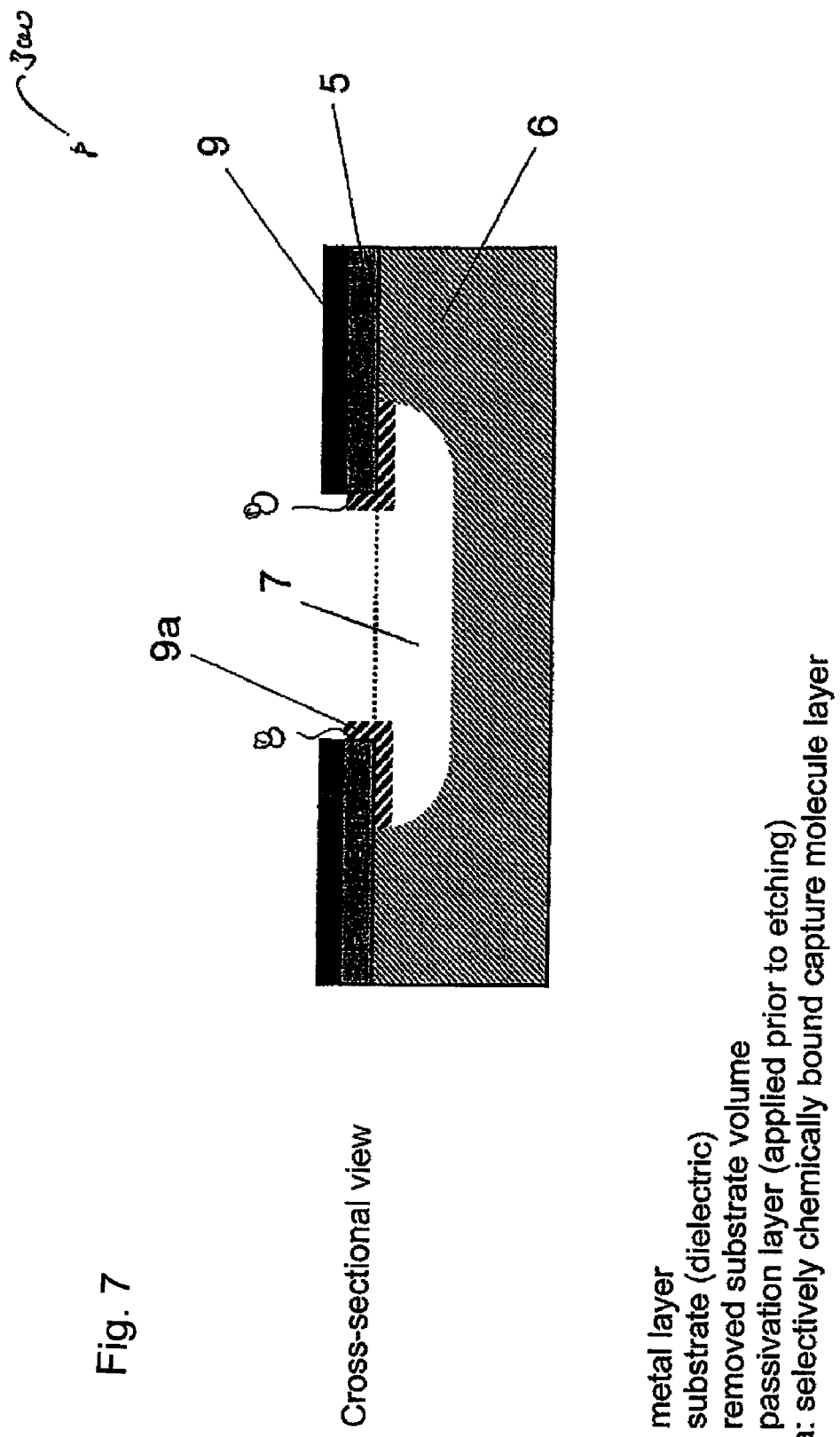
FIG. 7 is a side view of a THz structure in a third further embodiment of a surface sensor as a modification of the FIG. 4 embodiment.

FIG. 7 shows a third further embodiment of a modified THz structure 300 as compared to the second embodiment illustrated in FIG. 4. For the remainder, identical reference numerals have been used here for identical or similar features, respectively features having the same or an identical function.

In extension of the second embodiment, the metal layer 5 in the surface sensor 300 is covered by a non-precious metallic passivation layer 9 which suppresses or prevents chemical binding of the capture molecules. In the present case, the passivation layer 9 is applied to the metal layer 5 prior to the undercutting to release the slot edge 8. The passivation layer 9 in the form of a non-precious metallic layer is hence removed by being etched away together with the not further described metal layer 5 for forming the THz structure on the substrate 6 in regions 7 outside the THz structure, with the slot edge 8 thereby being released at the same time.

Figure 8:
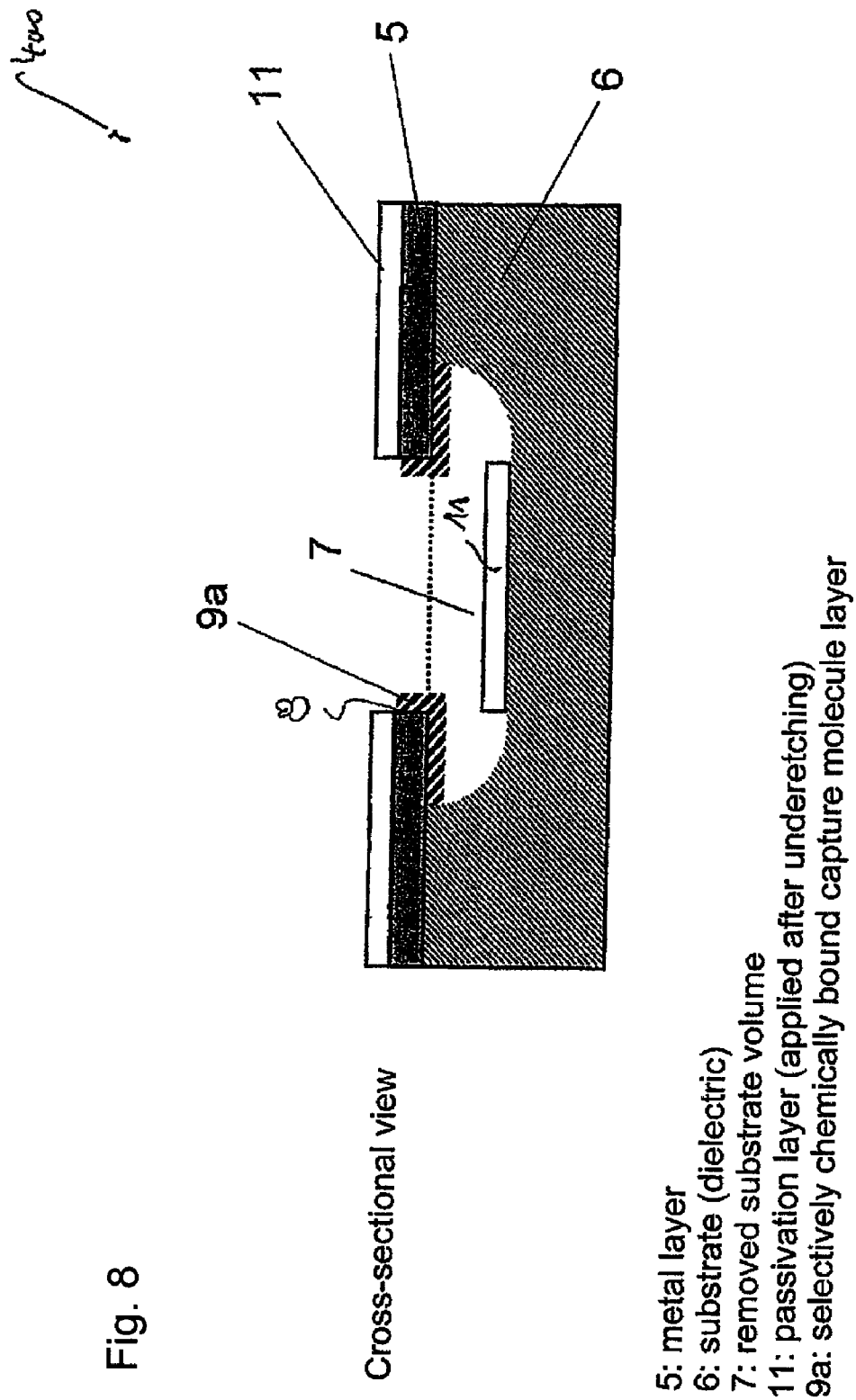
FIG. 8 is a side view of a THz structure in a fourth further embodiment of a surface sensor as a modification of the FIG. 4 embodiment.

FIG. 8 shows a further modification with respect to the second embodiment shown in FIG. 4 in the form of a fourth embodiment. In this case again, identical reference numerals have been used for reasons of simplicity for identical or similar features, respectively features having the same or an identical function.

Similar to FIG. 8, the passivation layer 11 is formed on the metal layer 5. The passivation layer 11 in the present case is realized in the form of an electrically insulating passivation layer, and is applied—in contrast to the process shown in FIG. 7—after the undercutting of slot edge 8. As a consequence, the passivation layer 11 is arranged on the substrate 6 also in the area 7 of the substrate volume removed by the undercutting process, i.e. inside of the THz structure not further described. Therefore, the present realization is suited as an electrically insulating passivation layer.

The third as well as the fourth embodiment of FIGS. 7 and 8 ensures that capture molecules as shown in the area 9a will only bind in the immediate area of the undercut slot edge 8 of the metal layer 5. The discussed application of the passivation layer 9, 11 will namely prevent an interaction between the capture molecules and the metal layer 5, respectively will only be possible in the area of the edge 8.

In summary, the invention relates to a surface sensor 100, 200, 300, 400, comprising a frequency-selective surface with periodically arranged THz structures 1 sensitive to THz radiation, in particular THz resonator structures 1, each having an associated polarization axis 3. In order to improve remote field characteristics, the invention provides for the asymmetrical configuration of a THz structure 1, and a group of two or more THz structures to have essentially centrosymmetrically aligned polarization axes for forming a unit cell.

It will be appreciated by those skilled in the art that changes could be made to the embodiments described above without departing from the broad inventive concept thereof. It is understood, therefore, that this invention is not limited to the particular embodiments disclosed, but it is intended to cover modifications within the spirit and scope of the present invention as defined by the appended claims.

I claim:

1. A surface sensor (100, 200, 300, 400), comprising a frequency-selective surface with periodically arranged THz structures (1) sensitive to THZ radiation, the THz resonator structures each having an associated polarization axis (3), wherein one THz structure (1) is configured asymmetrically, and a group of two or more THz structures have essentially centrosymmetrically aligned polarization axes (3) for forming a unit cell (10).

2. The surface sensor according to claim 1, wherein the group of two or more THz structures (1) forming a unit cell (10) is formed from THz structures initially arranged to be adjacent.

3. The surface sensor according to claim 1, wherein the THz structure (1) is a polar structure, the polar structure being one of a dipole structure, a tripole structure, a quadrupole structure, or a polystructure of a higher order.

4. The surface sensor according to claim 1, wherein a THz resonator structure (1) is realized in the form of an asymmetrically split ring resonator.

5. The surface sensor according to claim 1, wherein the unit cell (10) is formed by at least one mirroring of a THz structure (1).

6. The surface sensor according to claim 1, wherein there is an angle of 45° between a mirror axis (4a, 4b) and a polarization axis (3) of a THz structure in the unit cell (10).

7. The surface sensor according to claim 1, wherein the unit cell (10) comprises four THz structures (1).

8. The surface sensor according to claim 1, wherein a THz structure (1) is planar, and is metallically formed on a dielectric substrate (6).

9. The surface sensor according to claim 1, wherein the THz structure (1) is released from the substrate (6) at least at one edge (8), the at least one edge (8) being a slot edge.

10. The surface sensor (300, 400) according to claim 1, wherein the THz structure (1) is passivated except on one edge in such a manner that binding of a capture molecule (9a) is suppressed or prevented relative to the edge (8).

11. The surface sensor (300, 400) according to claim 10, wherein the passivation is realized in the form of a first passivation layer and a second passivation layer (9, 11), the first passivation layer (9) being only on the THz structure, the second passivation layer (11) being on and inside the THz structure.

12. The surface sensor according to claim 1, wherein the frequency-selective surface comprises a capture molecule.

13. A method for producing a surface sensor according to claim 1, wherein the frequency-selective surface with periodically arranged THz structures sensitive to THz radiation is formed by applying a THz structure to a surface via an inkjet process, and a biological capture molecule is applied via an inkjet process.

14. A system having a surface sensor according to claim 1, the system being a value document.

15. A method for detecting biological molecules utilizing the surface sensor of claim 1, wherein the biological molecules bind to known capture molecules having determined positions assigned on the sensor surface, and wherein the binding process changes resonance characteristics of the THz structures in a unit cell of an array of the frequency selective surface, the method comprising:
    irradiating the sensor surface with THz radiation; and
    measuring a change of resonance characteristics to detect the binding process.

\* \* \* \* \*